United States Patent [19]

Taylor

[11] 3,980,775

[45] Sept. 14, 1976

[54] COMPOUND FOR SKIN TREATMENT

[75] Inventor: Joseph Taylor, North Vancouver, Canada

[73] Assignee: Sebetrol Canada Inc., Vancouver, Canada

[22] Filed: Mar. 18, 1975

[21] Appl. No.: 559,583

[52] U.S. Cl. ............................... 424/167; 424/343; 424/346
[51] Int. Cl.² ............... A61K 31/00; A61K 31/045; A61K 31/05; A01N 9/00
[58] Field of Search .................... 424/167, 195, 196

[56] References Cited
OTHER PUBLICATIONS

Handbook of Non-Prescription Drugs (1973 Edition), published by Amer. Pharm. Assoc., Wash., D.C., pp. 157, 159, 163 & 165.

*Primary Examiner*—Donald B. Moyer
*Attorney, Agent, or Firm*—Carver and Company

[57] ABSTRACT

A synergistic compound containing liquor picis carbonis, resorcin, menthol, pure water and isopropanol.

5 Claims, No Drawings

COMPOUND FOR SKIN TREATMENT

BACKGROUND OF THE INVENTION

1. Field of the Invention

This invention relates to the treatment of skin diseases, particularly seborrheoa, psoriasis, pityriases, simplex and steatoides, simple dandruff and persistent scalp itch.

2. Prior Art

In the treatment of skin diseases, particularly disorders of the scalp, including seborrheoa, psoriasis, pityriases, simplex and steatoides, simple dandruff and persistent scalp itch, a variety of chemicals particularly resorcin, liquor picis carbonis and menthol have proven to be generally efficacious. Resorcin dissolved in alcohol and used in the treatment of scalp conditions has only been mildly successful. Liquor picis carbonis, in order to obtain only minor relief must be used in vast quantities and its odor and colour militate against its wider use. Menthol itself simply gives relief against itching and irritation.

SUMMARY OF THE INVENTION

The present invention provides a compound in which the healing properties of both liquor picis carbonis and resorcin are utilized. In the present invention these two chemicals together with menthol, pure water and alcohol provide a compound, the healing effect of which is much more pronounced than compounds using any of them separately.

A preferred mixture volumetric which is most efficacious is as follows:

| | |
|---|---|
| liquor picis carbonis | 2 percent |
| resorcin | 2 percent |
| menthol | 2 percent |
| pure water | 20 percent |
| isopropanol | 74 percent |
| (99 to 100 percent pure) | |

The menthol is added as a counter irritant and the pure water is added to inhibit drying of the skin.

It will be understood that although the proportions as specified foregoing are preferred, the proportions of liquor picis carbonis and resorcin and menthol can vary between 0.5 and 4 percent and the pure water between 5 and 20 percent.

The compound above is applied to the skin daily until the condition clears and then is applied two or three times a week for control.

There is no chemical reaction between the separate elements of the compound, however, the results achieved in its use when compared to results achieved by use of its components separately would indicate that the effectiveness is due to synergism.

I claim:

1. A synergistic compound for treatment of seborrheoa, psoriasis, pityriases, simplex, steatoides, simple dandruff and persistent scalp itch comprising a mixture, expressed in volumetric percentage, of

| | |
|---|---|
| liquor picis carbonis | .5 percent to 4.0 percent |
| resorcin | .5 percent to 4.0 percent |
| menthol | .5 percent to 4.0 percent |
| pure water | 5.0 percent to 20.0 percent |
| isopropanol | 68.0 percent to 95.5 percent. |

2. A synergistic compound as claimed in claim 1 in which liquor picis carbonis comprises 2 percent of the mixture.

3. A synergistic compound as claimed in claim 1 in which resorcin comprises 2 percent of the mixture.

4. A synergistic compound as claimed in claim 1 in which menthol comprises 2 percent of the mixture.

5. A synergistic compound as claimed in claim 1 in which liquor picis carbonis comprises 2 percent, resorcin comprises 2 percent, pure water comprises 20 percent and isopropanol comprises 74 percent of the mixture.

* * * * *